United States Patent [19]

Vecchietti et al.

[11] Patent Number: 5,441,956
[45] Date of Patent: Aug. 15, 1995

[54] HYDROISOQUINOLINE DERIVATIVES

[75] Inventors: Vittorio Vecchietti; Giulio Dondio; Silvano Ronzoni, all of Milan; Roberto Colle, Basiglio, all of Italy

[73] Assignee: Smithkline Beecham Farmaceutici S.p.A., Milan, Italy

[21] Appl. No.: 175,371

[22] PCT Filed: Jul. 1, 1992

[86] PCT No.: PCT/EP92/01483

§ 371 Date: Jan. 5, 1994

§ 102(e) Date: Jan. 5, 1994

[87] PCT Pub. No.: WO93/01186

PCT Pub. Date: Jan. 21, 1993

[30] Foreign Application Priority Data

Jul. 5, 1991 [IT] Italy .............................. MI91A1863
Mar. 11, 1992 [IT] Italy .............................. MI92A0563

[51] Int. Cl.⁶ ................ C07D 471/04; A61K 131/495
[52] U.S. Cl. .................... 514/250; 514/280; 514/283; 514/285; 544/343; 546/49; 546/53; 546/54; 546/56; 546/57; 546/62; 546/70
[58] Field of Search ..................... 546/49, 53, 54, 56, 546/57, 62, 70; 544/343; 514/250, 280, 285, 283

[56] References Cited

FOREIGN PATENT DOCUMENTS 0485636 5/1992 European Pat. Off. ............... 546/70
1436376 5/1976 United Kingdom ................ 546/139

*Primary Examiner*—Alan L. Rotman
*Assistant Examiner*—Zinna N. Davis
*Attorney, Agent, or Firm*—Charles M. Kinzig; Stephen Venetianer; Edward T. Lentz

[57] ABSTRACT

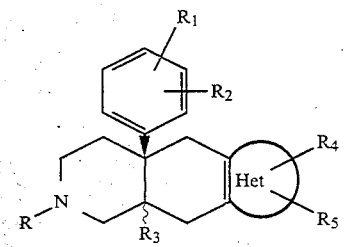

Compounds of formula (I) in which, R is linear or branched alkyl, cycloalkyl, cycloalkylalkyl, alkenyl, aryl, aralkyl or furan-2-yl alkyl; $R_1$ and $R_2$, which may be the same or different, are each hydrogen, hydroxy, alkoxy, or halogen; $R_3$ is hydrogen, hydroxy or alkoxy; "Het" is optionally substituted single or fused heteroxyclic ring, containing from 5 to 10 ring atoms and comprising up to four heteroatoms in the or each ring, selected from oxygen, nitrogen and sulphur; $R_4$ and $R_5$, which may be the same or different, are each hydrogen alkyl, halogen, nitro; CF, cyano, alkoxy carbonyl, NH, alkylcarbonylamino, hydroxy, alkoxy, or benzyl, are selective delta receptor agonists and are useful in the treatment of pain.

12 Claims, No Drawings

HYDROISOQUINOLINE DERIVATIVES

This application is a 371 of PCT/EP92/01483 filed on Jul. 1, 1992.

This invention is concerned with novel hydroisoquinoline derivatives, processes for their preparation, and their use in medicine.

The presence of at least three populations of opioid receptors (mu, delta and kappa) is now well established and documented and all three appear to be present in the central and peripheral nervous system of many species including man (Lord J. A. H. et al, Nature 1977, 267,495).

Activation of all 3 opioid receptor subtypes can lead to antinociception in animal models. In particular, studies with peptide delta agonists have indicated that activation of the delta receptor produces antinociception in rodents and primates, and can induce clinical analgesia in man (Yaksh T. L. and Onofrio, B. M. Lancet 1983, 1386). Some experiments suggest that these delta analgesics may also lack the usual side-effects associated with mu and kappa activation (Galligan et al, J. Pharm. Exp. Ther. 1984, 229, 641).

WO/8900995 discloses heterocycle condensed epoxymorphinan derivatives which are said to be delta selective antagonists, and EP-A-295783 discloses codeine derivatives which are said to be analgesic agents acting predominantly on delta receptors.

We have now discovered a novel class of heterocycle condensed octahydroisoquinoline derivatives which are selective delta opioid receptor ligands which may therefore be of potential therapeutic utility as analgesics.

According to the present invention, there is provided a compound, or a solvate or salt thereof of formula (I):

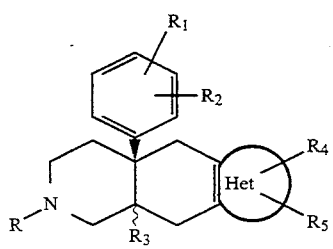

(I)

in which,

R is linear or branched $C_{1-5}$ alkyl, $C_{3-7}$ cycloalkyl, $C_{4-6}$ cycloalkylalkyl, $C_{3-5}$ alkenyl, aryl, aralkyl or furan-2-yl alkyl;

$R_1$ and $R_2$, which may be the same or different, are each hydrogen, hydroxy, $C_{1-3}$ alkoxy, preferably methoxy, or halogen;

$R_3$ is hydrogen, hydroxy or $C_{1-3}$ alkoxy, preferably methoxy;

"Het" is an optionally substituted single or fused heterocyclic ring, preferably having aromatic character, containing from 5 to 10 ring atoms and comprising up to four heteroatoms in the or each ring, selected from oxygen, hydrogen and sulphur;

$R_4$ and $R_5$, which may be the same or different, are each hydrogen, $C_{1-3}$ alkyl, preferably methyl, halogen, nitro, $CF_3$, cyano, $C_{1-3}$ alkoxy carbonyl, $NH_2$, $C_{1-3}$ alkylcarbonylamino, hydroxy, $C_{1-3}$ alkoxy, preferably methoxy, or benzyl.

When R is aryl, it is preferably phenyl, and when aralkyl, it is preferably phenyl $C_{1-6}$ alkyl.

Examples of R are methyl, ethyl, cyclopropylmethyl, propyl and 2-phenylethyl.

Examples of $R_1$ and $R_2$ are hydrogen, hydroxy and methoxy, in all positions of the aromatic ring.

Examples of 'Het' are indolo, N-methylindolo, N-ethylindolo, N-benzylindolo, benzofuro, benzothieno, quino and quinoxalino.

Examples of $R_4$ or $R_5$ are hydrogen, methyl, ethyl, fluorine, chlorine, hydroxy, methoxy, or benzyl.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additions ionic and solvent moieties must also be non-toxic.

Examples of pharmaceutically acceptable salts of a compound of formula (I) include acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of pharmaceutically acceptable solvates of a compound of formula (I) include hydrates.

The compounds of formula (I) may exist as cis or trans isomers, and the invention extends to both such forms as well as to their single enantiomers and to mixtures thereof, including racemates.

The present invention also provides a process for the preparation of a compound of formula (I) which comprises reacting a compound of formula (II):

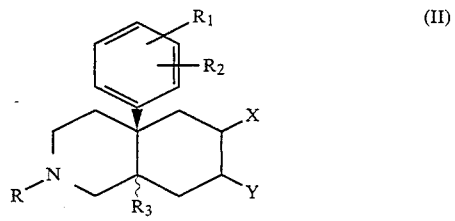

(II)

in which, simultaneously, one of X and Y is oxo and the other is hydrogen or oximino, and R, $R_1$, $R_2$ and $R_3$ are as defined for formula (I), with a compound of formula (III):

(III)

in which Het' is a ring-opened precursor of Het, as defined for formula (I), and $R_4$ and $R_5$ are as defined for formula (I), and optionally thereafter performing one or both of the following steps:
 a) converting the obtained compound of formula (I) to a further compound of formula (I),
 b) forming a salt and/or solvate of the obtained compound of formula (I).

Examples of the process of the invention are as follows:

i) To produce a compound of formula (I) in which Het is 2,3- or 3,2-indolo, 2,3- or 3,2-N-methylindolo, 2,3- or 3,2-benzofuro or 2,3- or 3,2-benzothieno, and $R_1$ and $R_2$ are other than hydroxy, a compound of formula (II) may be reacted with a compound of formula (IIIa):

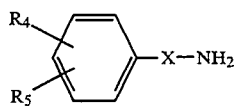
(IIIa)

in which X is —NH—, —NMe—, —S—, or —O— and $R_4$ and $R_5$ are as defined for formula (I), under Fischer condensation conditions.

ii) To produce a compound of formula (I) in which Het is N-methylindolo, N-ethylindolo, or N-benzylindolo, and $R_1$ and $R_2$ are than hydroxy, a corresponding compound of formula (I) in which Het is indolo may be reacted with a methyl, ethyl, or benzyl halide and a strong base (such as sodium or potassium hydride) in an aprotic solvent (such as THF or DMF).

iii) To produce a compound of formula (I) in which $R_1$ or $R_2$ is hydroxy, a compound of formula (I) in which $R_1$ or $R_2$ is methoxy is demethylated using a Lewis acid (such as $BBr_3$) or concentrated aqueous HI or HBr at elevated temperature, for example 25° to 110°.

iv) To produce a compound of formula (I) in which Het is 2,3 or 3,2quino and $R_1$ and $R_2$ are other than hydroxy, a compound of formula (II) may be reacted with a compound of formula (IIIb):

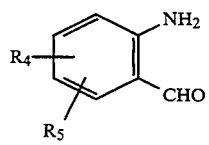
(IIIb)

in which $R_4$ and $R_5$ are as defined for formula (I), in the presence of methanesulfonic acid.

v) To produce a compound of formula (I) in which Het is 2,3 or 3,2-quinoxalino and $R_1$ and $R_2$ are other than hydroxy, a compound of formula (II) may be reacted with isoamyl nitrite and potassium tertbutoxide to obtain a compound of formula (IIa):

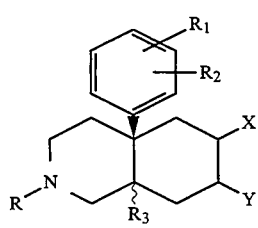
(IIa)

in which, simultaneously, one of X and Y is oxo and the other is oximino and R, $R_1$, $R_2$ and $R_3$ are as defined for formula (I).

The resulting compounds of formula (IIa) are thereafter condensed in refluxing DMF with a compound of formula (IIIc):

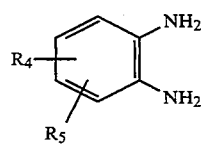
(IIIc)

in which $R_4$ and $R_5$ are as defined for formula (I).

Compounds of formula (II) in which X is oxo and Y is hydrogen are known compounds, or can be prepared from known compounds by known methods (Zimmerman D. et al, J. Org. Chem. 1989, 54, 1442).

Compounds of formula (II) in which X is hydrogen and Y is oxo are known compounds and can be prepared, for example, as described by Judd D. B. et al., J. Med. Chem,. 1992, 35, 48.

Alternatively, they may be prepared by a Robinson cyclisation reaction between a piperidine derivative of formula (IV):

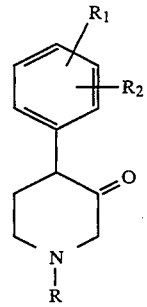
(IV)

in which R, $R_1$, and $R_2$ are as defined for formula (I), and methylvinylketone, and subsequent reduction with lithium in liquid ammonia, or catalytic hydrogenation.

Alternatively, these compounds of formula (II) can be prepared from compounds of formula (II) in which X is oxo and Y is hydrogen by using a 6,7-carbonyl shift technique according to methods known in the art.

Compounds of formula IV are known compounds or can be prepared from known compounds by known methods. (J.-C. S., Perk. Trans. I, 1989, 1187).

Compounds of formula (III) are commercially available compounds, or can be easily made from commercially available compounds.

As mentioned before, the compounds of formula (I) exist in more than one stereoisomeric form and the process of the invention produces mixtures thereof. The individual isomers may be Obtained from the enantiomerically pure intermediate of formula (II).

The individual forms of the compounds of formula (II) may be separated one from another by resolution using an optically active acid such as tartaric acid or 0,0'-di-p-toluoyltartaric acid. Alternatively, an asymmetric synthesis would offer a route to the individual form.

The compounds of formula (I) may be converted into their pharmaceutically acceptable acid addition salts by reaction with the appropriate organic or mineral acids.

Solvates of the compounds of formula (I) may be formed by crystallization or recrystallization from the appropriate solvent. For example hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

The activity of the compounds of formula (I) in standard tests indicates that they are of potential therapeutic utility in the treatment of pain.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinyl-pyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of pain in mammals, particularly humans, which comprises administering to the mammal in need of such treatment and/or prophylaxis an effective amount of a compound of formula (I) or a pharmaceutically acceptable salt or solvate thereof.

Compounds of this invention and their preparation are illustrated in the following Examples and their structures are summarised in Table I.

The preparation of novel intermediates is illustrated in the Descriptions.

DESCRIPTION 1

(−)-2-Ethyl-4aα-(3-methoxyphenyl)-1,2,3,4,4a, 5,6,7,8,8aβ-6-oxo-decahydroisoquinoline.

5.97 g (20.77 mmoles) of(±)-2-ethyl-4aα-(3-methoxyphenyl)-1,2,3,4, 4a,5,6,7,8,8aβ-6-oxo-decahydroisoquinoline were dissolved in 80 ml of abs. ethanol. 8.02 g (20.77 mmoles) of (+)-di-0,0'-p-toluoyl-D-tartaric acid, dissolved in 80 ml of abs. ethanol, were added to the hot solution of the free base.

After a gentle warming, the solution was filtered and the less soluble diastereomeric salt crystallized on standing. The salt was recrystallized from abs. ethanol, up to a constant rotatory power, to give 5.62 of (+)-di-0,0'-p-toluoyl-D-tartrate. M.P. = 161°–163° C.

$C_{38}H_{43}NO_{10}$ Elemental analysis: Calcd. C,67.74; H,6.43; N,2.08; Found C,67.30; H,6.47;N,2.03. $[\alpha]_D^{20}$ = +57.42 (C=2 in MeOH)

The tartrate salt was transformed into the free base by dissolving in 5% NaOH solution, extracting with $CH_2Cl_2$ and evaporating the solvent in vacuo to yield 2.3 g of the title compound (77% of the theoretical).

$[\alpha]_D^{20} = -83.85$ (C=2 in $CHCl_3$) The I.R. and N.M.R. spectra were identical to those obtained for the racemate.

DESCRIPTION 2

(+)-2-Ethyl-4aα-(3-methoxyphenyl)-1,2,3,4,4a, 5,6,7,8,8aβ-6-oxo-decahydroisoquinoline.

The mother liquors obtained from the first crystallization of Description 1 were evaporated in vacuo to dryness. The residue was treated with 5% NaOH solution and extracted with $CH_2Cl_2$ to afford 2.75 g (9.6 mmoles) of the enriched free base which was dissolved in 45 ml of abs. ethanol. 3.78 g (9.6 mmoles) of (−)-di-0-0'-p-toluoyl-L-tartaric acid, dissolved in 45 ml of abs. ethanol, were added to the hot solution of the free base and the diastereomeric salt crystallized on standing. The salt was recrystallized from ads. ethanol, up to a constant rotatory power, to give 5.82 g of (−)-di-0-0'-p-toluoyl-L-tartrate. M.P. = 162°–163° C.

$C_{38}H_{43}NO_{10}$ Elemental analysis: Calcd. C,67.74; H,6.43; N,2.08; Found C,67.42; H,6.41; N,2.05. $[\alpha]_D^{20} = -55.36$ (C=2 in MeOH)

The tartrate salt was transformed into the free base dissolving in 5% NaOH solution, extracting with $CH_2Cl_2$ and evaporating the solvent in vacuo to yield 2.4 g of the title compound (80% of the theoretical).

$[\alpha]_D^{20} +82.20$ (C=2 in $CHCl_3$) The I.R. and N.M.R. spectra were identical to those obtained for the racemate.

EXAMPLE 1

2-ethyl-4aα-(3-hydroxyphenyl)-1,2,3,4,4a,5,11,11aβ-octahydro indolo[2,3-g]isoquinoline hydrochloride To a stirred solution of 0.493 ml (5.22 mmoles) of boron tribromide in 15 ml of dry chloroform was added dropwise, under nitrogen at room temperature, a solution of 313 mg (0.868 mmoles) of 2-ethyl-4aα-(3-methoxyphenyl)-1,2,3,4,4a,5,11,11aβ-octahydro indolo[2,3-g]isoquinoline in 3 ml of dry chloroform.

After 30 min the solution was poured into 15 g of ice containing 1.5 ml of concentrated $NH_4OH$ and stirred for 30 min. The precipitate was filtered and collected. The filtrate was extracted with $CH_2Cl_2$, dried over sodium sulphate, evaporated in vacuo and combined with the precipitate.

The solid residue was chromatographed by silica gel flash column chromatography, eluting with a mixture of $CH_2Cl_2$/MeOH/conc. $NH_4OH$ 79:15:1 respectively, to yield 108 mg of solid which was taken up in 5 ml of methanol and brought to acidic pH with $HCl/Et_2O$. The precipitate was filtered, washed and dried, to yield 60 mg of the title compound. M.P. = 277°–278° C.

$C_{23}H_{26}N_2O$ .HCl Elemental analysis: Calcd C,72.14; H,7.11; N,7.32; Cl,9.26; Found C,71.69; H,7.01; N,7.25; Cl,9.00. I.R. (KBr): 3450; 3260; 3200; 1600; 1450 $cm^{-1}$

EXAMPLE 2

2-methyl-4aα-(3-hydroxyphenyl)-1,2,3,4,4a,5,11,11aα-octahydro indolo[2,3-g]isoquinoline 250 mg (0.72 mmoles) of 4aα-(3-methoxyphenyl)-1,2,3,4,4a,5,11,11aα-octahydro indolo[2,3-g]isoquinoline were reacted with 0.4 ml (4.32 mmoles) of boron tribromide as described in Example 1. The solid residue was purified by silica gel flash column chromatography, eluting with a mixture of $CH_2Cl_2$/MeOH/conc. $NH_4OH$, 86:10:0.6 respectively, obtaining 180 mg of the title compound. M.P. = 200°–207° C.

$C_{22}H_{24}N_2O$ Elemental analysis: Calcd. C, 79.48; H, 7.28; N, 8.43; Found C, 79.09; H, 7.11; N, 8.21. I.R. (KBr): 3400; 3280; 2900; 1595; 1470 $cm^{-1}$

EXAMPLE 3

2-ethyl-4aα-(3-methoxyphenyl)-1,2,3,4,4a,5,11,11aβ-octahydro indolo[2,3-g]isoquinoline hydrochloride 532 mg (1.64 mmoles) of 2-ethyl-4aα-(3-methoxyphenyl)-1,2,3,4,4a,5,6,7,8,8aβ-6-oxo-decahydroisoquinoline hydrochloride and 357 mg (2.47 mmoles) of phenylhydrazine hydrochloride were dissolved in 33 ml of methanol saturated with HCl. The solution was refluxed under a nitrogen atmosphere for 3 hours and then cooled at room temperature.

The reaction mixture was evaporated in vacuo, the residue was dissolved in ethyl acetate and treated with an excess of 1N sodium hydroxide, then the mixture was extracted with ethyl acetate. The combined extracts were dried over sodium sulphate and evaporated in vacuo.

The solid residue was chromatographed by silica gel flash column chromatography, eluting with a mixture of $CH_2Cl_2$/MeOH/conc. $NH_4OH$ 94:5:0.5 respectively, to yield 457 mg of the free base which was taken up in 10 ml of acetone and brought to acidic pH with $HCl/Et_2O$.

The precipitate was filtered, washed and dried, to yield 400 mg of the title compound. M.P. = 168°–171° C.

$C_{24}H_{28}N_2O$ .HCl Elemental analysis: Calcd. C,72.61; H,7.36; N,7.06; Cl,8.93; Found C,72.35; H,7.25; N,6.99;

Cl,8.75. I.R. (KBr): 3400; 3200; 1605; 1460 cm$^{-1}$ N.M.R. (CDCl$_3$) 300 MHz (free base): δ8.10 (s broad, 1H); 7.45 (m, 1H); 7.20 (m, 1H); 7.08 (m, 5H); 6.62 (m, 1H); 3.68 (s, 3H); 2.85–3.10 (m, 6H); 2.58 (m, 2H); 2.45 (m, 3H); 2.00 (m, 2H); 1.10 (t, 3H).

EXAMPLE 4

4aα-(3-methoxyphenyl)-2-methyl-1,2,3,4,4a,5,11,11aα-octahydro indolo[2,3-g]isoquinoline 500 mg (1.83 mmoles) of 2-methyl-4aα-(3-methoxyphenyl)-1,2,3,4,4a,5,6,7,8,8aα-6-oxo-decahydroisoquinoline and 396 mg (2.74 mmoles) of phenylhydrazine hydrochloride were reacted as described in Example 3.

After the work-up, the solid residue was chromatographed by silica gel flash column chromatography, eluting with a mixture of CH$_2$Cl$_2$/MeOH/conc. NH$_4$OH 100:3:0.3 respectively, to yield 250 mg of the title compound. M.P.=202°–206° C.

C$_{23}$H$_{26}$N$_2$O Elemental analysis: Calcd. C,79.73; H,7.56; N,8.09; Found C,79.50; H,7.31; N,7.88. I.R. (KBr): 3400; 3120; 2790; 1600; 1580 cm$^{-1}$ N.M.R. (CD$_3$OD) 300 MHz: δ7.3–6.65 (m, 8H); 3.67 (s, 3H); 3.33 (m, 1H); 3.03 (m, 1H); 2.88 (m, 1H); 2.73 (m, 1H); 2.59 (m, 1H); 2.51 (m, 1H); 2.40–2.20 (m, 7H); 1.63 (m, 1H).

EXAMPLE 5

2-Methyl-4aα-(3-hydroxyphenyl)-1,2,3,4,4a,5,11,11aβ-octahydroindolo[2,3-g]isoquinoline hydrochloride.

1.92 g (5.54 mmoles) of 2-methyl-4aα-(3-methoxyphenyl)-1,2,3,4,4a,5,11,11aβ-octahydroindolo[2,3-g]isoquinoline were reacted with 3.14 ml (33.24 mmoles) of boron tribromide as described in Example 1. The solid residue was taken up in MeOH and brought to acidic pH with HCl/Et$_2$O. The precipitate was filtered, washed and dried to yield 1.4 g of the title compound. M.P.=>300° C.

C$_{22}$H$_{24}$N$_2$O.HCl Elemental analysis: Calcd. C,71.62; H,6.83; N,7.59; Cl,9.61; Found C,66.94; H,6.53; N,6.92; Cl,8.96. I.R. (KBr): 3420; 3250; 2600; 1580; 1460 cm$^{-1}$

EXAMPLE 6

2-Methyl-4aα-(3-methoxyphenyl)-1,2,3,4,4a,5,11,11aβ-octahydroindolo[2,3-g]isoquinoline hydrochloride hemihydrate.

6.0 g (19.36 mmoles) of 2-methyl-4aα-(3-methoxyphenyl)-1, 2,3,4,4a, 5,6,7,8,8aβ-6-oxo-decahydroisoquinoline hydrochloride and 4.2 g (29.04 mmoles) of phenylhydrazine hydrochloride were reacted and worked-up as described in Example 3. The solid residue was purified by silica gel flash column chromatography, eluting with a mixture of CH$_2$Cl$_2$/MeOH/conc. NH$_4$OH 90:7:0.7 respectively,to afford 3.68 g of the free base which was taken up in a mixture of acetone/methanol 1:1 and brought to acidic pH with HCl/Et$_2$O. The precipitate was filtered, washed and dried to yield 3.1 g of the title compound. M.P.=>300° C.

C$_{23}$H$_{26}$N$_2$O.HCl.½H$_2$O Elemental analysis: Calcd. C,70.48; H,7.20; N,7.15; Cl,9.05; Found C,70.41; H,7.25; N,6.99; Cl,9.04. I.R. (KBr): 3410; 3150; 1605; 1580; 1465; 1040 cm$^{-1}$ N.M.R. (DMSO-d6) 80 MHz: δ10.6 (s,1H); 7.4–6.8 (m,9H); 3.7 (s,3H); 3.5–2.6 (m,11H); 2.5 (s,3H).

EXAMPLE 7

2,6-Dimethyl-4aα-(3-hydroxyphenyl)-1,2,3,4,4a,5,11,-11aβ-octahydroindolo[2,3-g]isoquinoline.

950 mg (2.63 mmoles) of 2,6-dimethyl-4aα-(3-methoxyphenyl)-1,2,3,4,4a,5,11,11aβ-octahydroindolo[2,3-g]isoquinoline were reacted with 1.5 ml (15.8 mmoles) of boron tribromide as described in Example 1. The solid residue was purified by silica gel flash column chromatography, eluting with a mixture of CH$_2$Cl$_2$/MeOH/conc. NH$_4$OH 86:10:0.6 respectively, to yield 130 mg of the title compound. M.P.=252°–254° C.

C$_{23}$H$_{26}$N$_2$O I.R. (KBr): 3420; 1580; 1470; 1235 cm$^{-1}$ N.M.R. (CD$_3$OD) 80 MHz: δ7.5–6.4 (m,8H); 3.5 (s,3H); 3.4–2.1 (m,11H); 2.35 (s,3H).

EXAMPLE 8

2,6-Dimethyl-4aα-(3-methoxyphenyl)-1,2,3,4,4a,5,11,-11aβ-octahydroindolo[2,3-g]isoquinoline.

A solution of 200 mg (0.58 mmoles) of 2-methyl-4aα-(3-methoxyphenyl)-1, 2,3,4,4a,5,11,11aβ-octahydroindolo[2,3-g]isoquinoline, dissolved in 2 ml of dimethylformamide, was added dropwise, under nitrogen atmosphere at 0° C., to a suspension of 26 mg (0,65 mmoles) of 60–65% NaH dispersion in mineral oil in 2 ml of dimethylformamide. The mixture was stirred 1 hour at 0° C., then 0.04 ml (0.65 mmoles) of methyl iodide were added dropwise and the reaction mixture was allowed to reach room temperature. After 40 minutes the solvent was evaporated in vacuo and the residue was taken-up in H$_2$O and extracted with CH$_2$Cl$_2$. The combined extracts were dried over Na$_2$SO$_4$ and evaporated in vacuo to dryness.

The residue was purified by silica gel flash column chromatography, eluting with a mixture of (i-Pr)$_2$O/MeOH/conc. NH$_4$OH 85:15:0.4 respectively, to yield 50 mg of the title compound. Mop.=128°–130° C.

C$_{24}$H$_{28}$N$_2$O I.R. (KBr): 2910; 1610; 1580; 1470; 1240 cm$^{-1}$ N.M.R. (CDCl$_3$) 80 MHz: δ7.4–6.9 (m,7H); 6.8–6.5 (m,1H); 3.65 (s,3H); 3.5 (s,3H); 3.3–2.1 (m,11H); 2.35 (s,3H).

EXAMPLE 9

2-Methyl-4aα-phenyl-1,2,3,4,4a,5, 11,11aβ-octahydroindolo[2,3-g]isoquinoline.

873 mg (6.31 mmoles) of potassium carbonate and 798 mg (4.42 mmoles) of 1-phenyl-5-chlorotetrazole were added to a solution of 1.4 g (4.21 mmoles) of 2-methyl-4aα-(3-hydroxyphenyl)-1, 2,3,4,4a,5,11,11aβ-octahydroindolo[2,3-g]isoquinoline in 20 ml of dimethylformamide under nitrogen atmosphere at room temperature. The reaction mixture was heated overnight a 70° C., the solvent was evaporated in vacuo and the residue was taken up in H$_2$O and extracted with EtOAc. The combined extracts were dried over Na$_2$SO$_4$ and evaporated in vacuo ro dryness.

The crude product was purified by silica gel flash column chromatography, eluting with a mixture of CH$_2$Cl$_2$/MeOH/conc. NH$_4$OH 86:10:0.6 respectively to yield 1.0 g of 2-methyl-4aα-[3-[(1-phenyltetrazol-5-yl) oxy ]phenyl ]-1,2,3,4,4a,5,11,11aβ-octahydroindolo[2,3-g]isoquinoline. M.P.=110°–115° C.

C$_{29}$H$_{28}$N$_6$O Elemental analysis: calcd. C,73.08; H,5.92; N,17.64; Found C,71.68; H,5.97; N,17.21. I.R. (KBr): 3400; 3200; 3080; 1600; 1590; 1500; 1450 cm$^{-1}$ N.M.R. (CDCl$_3$) 80 MHz: δ7.8–6.9 (m,13H); 3.1–2.0 (m,11H); 2.35 (s,3H).

This intermediate was dissolved in 35 ml of glacial acetic acid and hydrogenated at 60° C. in a Parr apparatus at 60 psi in the presence of a catalytic amount of 10% Pd on charcoal, until the theoretical amount of H$_2$ was consumed. The catalyst was filtered off and the solvent was evaporated in vacuo. The residue was taken up in H$_2$O, brought to basic pH with an excess of 40% NaOH and extracted with EtOAc. The combined extracts were dried over Na$_2$SO$_4$ and evaporated in vacuo to dryness. The crude product was purified by silica gel flash column chromatography, eluting with a mixture of CH$_2$Cl$_2$/MeOH/conc. NH$_4$OH 90:8:0.5 respectively, to yield 100 mg of the title compound. M.P.=221°–223° C.

C$_{22}$H$_{24}$N$_2$ I.R. (KBr): 3200; 2940; 1470; 1455; 1280 cm$^{-1}$ N.M.R. (CDCl$_3$) 80 MHz: 7.7 (s broad,1H); 7.45–6.85 (m,9H); 3.0–1.9 (m,11H); 2.35 (s,3H).

EXAMPLE 10

2-Methyl-4aα-(3-hydroxyphenyl)-1,2,3,4,4a,5, 11, 11aβ-octahydrobenzofuro[2,3-g]isoquinoline.

900 mg (2.59 mmoles) of 2-methyl-4aα-(3-methoxyphenyl)-1,2,3,4,4a,5,11,11aβ-octahydrobenzofuro[2,3-g]isoquinoline were reacted with 1.47 ml (15.5 mmoles) of boron tribromide as described in Example 1. The crude product was purified by silica gel flash column chromatography, eluting with a mixture of CH$_2$Cl$_2$/MeOH/conc. NH$_4$OH 86:10:0.6 respectively, to yield 550 mg of the title compound. M.P.=258°–261° C.

C$_{22}$H$_{23}$NO$_2$ Elemental analysis: Calcd. C,79.25; H,6.95; N,4.20; Found C,76.81; H,6.86; N,4.05. I.R. (KBr): 3440; 2910; 1590; 1450; 1240; 1230 cm$^{-1}$ N.M.R. (DMSO-d6) 80 MHz: δ9.1 (s,1H); 7.5–6.4 (m,8H); 3.5–2.1 (m,11H); 2.35 (s,3H).

EXAMPLE 11

2-Methyl-4aα-(3-methoxyphenyl)-1,2,3,4,4a,5,11,-11aβ-octahydrobenzofuro[2,3-g]isoquinoline hydrochloride.

3.90 g (26.8 mmoles) of O-phenylhydroxylamine hydrochloride and 3.28 ml (50.64mmoles) of methanesulfonic acid were added to a solution of 3.92 g (12.66 mmoles) of 2-methyl-4aα-(3-methoxyphenyl)-1,2,3,4,4a,5,6,7,8,8aβ-6-oxo-decahydroisoquinoline hydrochloride in 240 ml of absolute ethanol and refluxed for 2 hours under nitrogen atmosphere. The reaction mixture was evaporated in vacuo; the residue was taken up in H$_2$O, brought to basic pH with an excess of 20% NaOH and extracted with EtOAc. The combined extracts were dried over Na$_2$SO$_4$ and evaporated in vacuo to dryness. The solid residue was purified by silica gel flash column chromatography, eluting with a mixture of CH$_2$Cl$_2$/MeOH/conc. NH$_4$OH 94.5:5:0.5 respectively, to yield 1.2 g of the free base, which was taken up in acetone and the solution brought to acidic pH with HCl/Et$_2$O. The precipitate was filtered, washed and dried to yield 900 mg of the title compound. M.P.=246°–248° C.

C$_{23}$H$_{25}$NO$_2$.HCl Elemental analysis: Calcd. C,71.95; H,6.83; N,3.65; Cl,9.24; Found C,69.22; H,6.59; N,3.53; Cl,10.10. I.R. (KBr): 3430; 2400; 1600; 1580; 1450 cm$^{-1}$ MS (E.I.) (free base): :347 (M+); 203. N.M.R.(CDCl$_3$) 300 MHz (free base): δ7.3–6.5 (m,8H); 3.53 (s,3H); 3.15 (d,1H); 2.8–2.75 (m,4H); 2.65 (d,1H); 2.35–2.15 (m,3H); 2.25 (s,3H); 1.35 (m,2H).

EXAMPLE 12

2,9-Dimethyl-4aα-(3-hydroxyphenyl)-1,2,3,4,4a,5,11,-11aβ-octahydroindolo[2,3-g]isoquinoline.

820 mg (2.07 mmoles) of 2,9-dimethyl-4aα-(3-methoxyphenyl)-1, 2,3,4,4a,5,11,11aβ-octahydroindole[2,3-g]isoquinoline were reacted with 1.2 ml (12.42 mmoles) of boron tribromide as described in Example 1.

The solid residue was crystallized from 40 ml of a mixture of acetone/MeOH 9:1 respectively.

The precipitate was filtered, washed and dried, to yield 288 mg of the title compound. M.P.=292°–296° C.

C$_{23}$H$_{26}$N$_2$O I.R. (KBr): 3210; 1610; 1460 cm$^{-1}$ N.M.R. (DMSO-d6) 80 MHz: δ6.45–7.20 (m,8H); 3.95–4.45 (m,2H); 2.85 (s,3H); 2.38 (s,3H); 2.00–3.80 (m,10H).

EXAMPLE 13

2,9-Dimethyl-4aα-(3-methoxyphenyl)-1,2,3,4,4a,5,11,-11aβ-octahydroindolo[2,3-g]isoquinoline hydrochloride.

1.5 g (4.84 mmoles) of 2-methyl-4aα-(3-methoxyphenyl)-1, 2,3,4,4a,5,6,7,8,8aβ-6-oxo-decahydroisoquinoline hydrochloride and 0.77 g (4.84 mmoles) of p-tolylhydrazine hydrochloride were reacted as described in Example 3.

The reaction mixture was evaporated in vacuo; the residue was dissolved in a mixture of CH$_2$Cl$_2$ and 1N NaOH and extracted with CH$_2$Cl$_2$. The combined extracts were dried over Na$_2$SO$_4$ and evaporated in vacuo to dryness.

The solid residue was taken up in MeOH and brought to acidic pH with HCl/Et$_2$O. The precipitate was filtered, washed and dried to yield 1.1 g of the title compound. M.P.=245°–250° C.

C$_{24}$H$_{28}$N$_2$O.HCl Elemental analysis: Calcd. C,72.60; H,7.36; N,7.05; Found C,70.69; H,7.45; N,6.73. I.R. (KBr): 3410; 3210; 1600; 1470; 1250 cm$^{-1}$ N.M.R. (CD$_3$OD) 80 MHz: δ7.5–6.6 (m,8H); 3.6 (s,3H); 3.4–2.3 (m,11H); 2.7 (s,3H); 2.4 (s,3H).

EXAMPLE 14

2-Methyl-4aα-(3-hydroxyphenyl)-9-fluoro-1,2,3,4,4a,5,11,11aβ-octahydroindolo[2,3-g]isoquinoline.

1.1 g (3.0 mmoles) of 2-methyl-4aα-(3-methoxyphenyl)-9-fluoro-1,2,3,4,4a,5,11,11aβ-octahydroindolo[2,3-g]isoquinoline were reacted with 1.7 ml (18.0 mmoles) of boron tribromide as described in Example 1.

The solid residue was crystallized from MeOH. The precipitate was filtered, washed and dried, to yield 580 mg of the title compound. M.P.=>300° C.

C$_{22}$H$_{23}$FN$_2$O Elemental analysis: Calcd. C,75.40; H,6.61; N,7.99; F,5.42; Found C,73.63; H,6.46; N,7.77; F,5.29. I.R. (KBr): 3280; 2940; 1595; 1460; 1255 cm$^{-1}$

EXAMPLE 15

2-Methyl-4aα-(3-methoxyphenyl)-9-fluoro-1,2,3,4,4a,5,11,11aβ-octahydroindolo[2,3-g]isoquinoline hydrochloride.

1.5 g (4.84 moles) of 2-methyl-4aα-(3-methoxyphenyl)-1,2,3,4,4a,5,6,7,8,8aβ-6-oxo-decahydroisoquinoline hydrochloride and 0.79 g (4.84 moles) of 4-fluorophenylhydrazine hydrochloride were reacted as described in Example 3 to yield 1.47 g of the title compound which was recrystallized from MeOH. M.P.=>300° C.

C$_{23}$H$_{25}$FN$_2$O.HCl Elemental analysis: Calcd. C,68.90; H,6.53; N,6.98; Cl,8.84; F,4.73; Found C,68.81; H,6.56; N,6.83; Cl,8.83; F,4.62. I.R. (KBr): 3440; 3200; 1605; 1455 cm$^{-1}$

EXAMPLE 16

2-Methyl-4aα-(3-hydroxyphenyl)-7-chloro-1,2,3,4,4a,5,11,11aβ-octahydroindolo[2,3-g]isoquinoline.

600 mg (1.58 mmoles) of 2-methyl-4aα-(3-methoxyphenyl)-7-chloro-1,2,3,4,4a,5,11,11aβ-octahydroindolo[2,3-g]isoquinoline were reacted with 0.9 ml (9.48 mmoles) of boron tribromide as described in Example 1.

The solid residue was crystallized from MeOH. The precipitate was filtered, washed and dried to yield 200 mg of the title compound. M.P.=>300° C.

C$_{22}$H$_{23}$ClN$_2$O Elemental analysis: Calcd. C.72.02; H,6.32; N,7.64; Cl,9.66; Found C,70.42; H,6.25; N,7.38; Cl,9.36. I.R. (KBr): 3250; 2850; 1590; 1450; 1245 cm$^{-1}$

EXAMPLE 17

2-Methyl-4aα-(3-methoxyphenyl)-7-chloro-1,2,3,4,4a,5,11,11aβ-octahydroindolo[2,3-g]isoquinoline hydrochloride.

1.5 g (4.84 mmoles) of 2-methyl-4aα-(3-methoxyphenyl)-1, 2,3,4,4a,5,6,7,8,8aβ-6-oxo-decahydroisoquinoline hydrochloride and 0.87 g (4.84 mmoles) of 2-chlorophenylhydrazine hydrochloride were reacted and worked-up as described in Example 3.

The solid residue was purified by silica gel flash column chromatography, eluting with a mixture of CH$_2$Cl$_2$/MeOH/conc. NH$_4$OH 86:10:0.6 respectively, to yield 1.2 g of the free base which was taken up in 50 ml of acetone and the solution brought to acidic pH with HCl/Et$_2$O.

The precipitate was filtered, washed and dried, to yield 920 mg of the title compound. M.P.=>300° C.

C$_{23}$H$_{25}$ClN$_2$O.HCl Elemental analysis: Calcd. C,66.18; H,6.28; N,6.71; Cl16.99; Found C,64.58; H,6.11; N,6.51; Cl,15.89. I.R. (KBr): 3420; 3205; 2480; 1600; 1470; 1250 cm$^{-1}$ N.M.R. (CD$_3$OD) 80 MHz: δ7.4–6.6 (m,8H); 3.65 (s,3H); 3.6–2.5 (m,11H); 2.85 (s,3H).

EXAMPLE 18

2-Methyl-4aα-(3-hydroxyphenyl)-9-chloro-1,2,3,4,4a,5,11,11aβ-octahydroindolo[2,3-g]isoquinoline hydrochloride.

960 mg (2.5 mmoles) of 2-methyl-4aα-(3-methoxyphenyl)-9-chloro-1,2,3,4,4a,5,11,11aβ-octahydroindolo[2,3-g]isoquinoline were reacted with 1.4 ml (15 mmoles) of boron tribromide as described in Example 1.

The solid residue was taken up in MeOH and the solution brought to acidic pH with HCl/Et$_2$O. The precipitate was filtered, washed and dried to yield 410 mg of the title compound. M.P.=>300° C.

C$_{22}$H$_{23}$ClN$_2$O.HCl Elemental analysis: Calcd. C,65.50; H,5.99; N,6.94; Cl,17.50; Found C,61.39; H,5.71; N,6.40; Cl,16.88. I.R. (KBr): 3410; 3210; 1580; 1460 cm$^{-1}$ N.M.R. (DMSO-d$_6$) 80 MHz: δ66.50.7.60 (m,8H); 3.95–4.45 (m,2H); 2.95 (s,3H); 1.90–3.90 (m,10H).

EXAMPLE 19

2-Methyl-4aα-(3-methoxyphenyl)-9-chloro-1,2,3,4,4a,5,11,11aβ-octahydroindolo[2,3-g]isoquinoline hydrochloride.

1.5 g (4.84 mmoles) of 2-methyl-4aα-(3-methoxyphenyl)-1, 2,3,4,4a,5,6,7,8,8a β-6-oxo-decahydroisoquinoline hydrochloride and 0.87 g (4.84 mmoles) of 4-chlorophenylhydrazine hydrochloride were reacted as described in Example 3.

The solvent was evaporated in vacuo and the solid residue was recrystallized from MeOH. The precipitate was filtered, washed and dried to yield 1.2 g of the title compound. M.P.=>300° C.

C$_{23}$H$_{25}$ClN$_2$O.HCl Elemental analysis: Calcd. C,66.10; H,6.27; N,6.71; Cl,16.90; Found C,64.52; H,6.11; N,6.59; Cl,16.58. I.R (KBr): 3340; 2920; 1600; 1500; 1330 cm$^{-1}$ N.M.R (CD$_3$OD) 80 MHz: δ7.4–6.6 (m,3H); 4.0–2.4 (m,11H); 3.65 (s,3H); 2.75 (s,3H).

EXAMPLE 20

2-Ethyl-6-methyl-4aα-(3-methoxyphenyl)-1,2,3,4,4a,5,11,11aβ-octahydroindolo[2,3-g]isoquinoline hydrochloride.

900 mg (2.5 mmoles) of 2-ethyl-4aα-(3-methoxyphenyl)-1,2,3,4,4a,5,11,11aβ-octahydroindolo[2,3-g]isoquinoline, 66 mg (2.8 mmoles) of 60–65% NaH and 0.171ml(2.75 mmoles) of methyliodide were reacted as described in Example 8.

After the work-up the residue was Purified by silica gel flash column chromatography, eluting with a mixture of CH$_2$Cl$_2$/MeOH/conc. NH$_4$OH 94.5:5:0.5respectively, to yield 550 mg of the free base which was taken-up in acetone and brought to acidic pH with HCl/Et$_2$O. The precipitate was filtered, washed and dried to yield 450 mg of the title compound. M.P.=234°–240° C.

C$_{25}$H$_{30}$N$_2$O.HCl I.R. (KBr): 3310, 2940, 2405, 1610, 1580, 1470 cm$^{-1}$ Elemental analysis: Calcd. C,73.06; H,7.60; N,8.63; Cl,6.82; Found C,72.28; H,7.57; N,8,82; Cl,6.68.

EXAMPLE 21

2-Ethyl-6-methyl-4aα-(3-hydroxyphenyl)-1,2,3,4,4a,5,11,11aβ-octahydroindolo[2,3-g]isoquinoline hydrochloride.

410 mg (1.13 mmoles) of 2-ethyl-6-methyl-4aα-(3-methoxyphenyl)-1,2,3,4,4a,5,11,11aβ-octahydroindolo[2,3-g]isoquinoline were reacted with 0.64 ml (6.8 mmoles) of boron tribromide as described in Example 1. The solid residue was purified by silica gel flash column chromatography, eluting with a mixture of CH$_2$Cl$_2$/MeOH/conc. NH$_4$OH 86:10:0.6 respectively. The product was dissolved in MeOH and brought to acidic pH with HCl/Et$_2$O. The precipitate was filtered, washed and dried to yield 200 mg of the title compound. M.P.=>300° C.

C$_{24}$H$_{28}$N$_2$O.HCl I.R. free base (KBr): 3420; 1580; 1470; 1230 cm$^{-1}$

EXAMPLE 22

2-Methyl-4aα-phenyl-9-methoxy-1,2,3,4,4a,5,11,11aβ-octahydroindolo[2,3-g]isoquinoline.

900 mg (3.22 mmoles) of 2-methyl-4aα-phenyl-1,2,3,4,4a,5,6,7,8,8aβ-6-oxo-decahydroisoquinoline hydrochloride and 562 mg (3.22 mmoles) of 4-methoxyphenylhydrazine hydrochloride were reacted and worked-up as described in Example 3.

The solid residue was purified by silica gel flash column chromatography, eluting with a mixture of CH$_2$Cl$_2$/MeOH/conc. NH$_4$OH 93:7:0.5 respectively, to afford 600 mg of the pure free base which was crystallized from AcOEt. The precipitate was filtered, washed and dried to yield 400 mg of the title compound. M.P.=201°-203° C.

C$_{23}$H$_{26}$N$_2$O I.R. (KBr): 3410; 2930; 1625; 1595; 1465 cm$^{-1}$ Elemental analysis: Calcd. C,79.73; H,7.56; N,8.09; Found C,79.74; H,7.58; N,8.05.

EXAMPLE 23

2-Methyl-4aα-phenyl-9-hydroxy-1,2,3,4,4a,5,11,-11aβ-octahydroindolo[2,3-g]isoquinoline.

1.6 g (4.6 mmoles) of 2-methyl-4aα-phenyl-9-methoxy-1,2,3,4,4a,5,11,11aβ-octahydroindolo[2,3-g]isoquinoline were reacted with 2.6 ml (27.6 mmoles) of boron tribromide as described in Example 1. The solid residue was purified by silica gel flash column chromatography, eluting with CH$_2$Cl$_2$/MeOH/conc. NH$_4$OH 87:13:0.8 respectively. The product was dissolved in MeOH and brought to acidic pH with HCl/Et$_2$O. The precipitate was filtered, washed and dried to yield 200 mg of the title compound. M.P.=>300° C.

C$_{22}$C$_{24}$N$_2$O.HCl I.R. (KBr): 3470; 3250; 2940; 1630; 1595 cm$^{-1}$ Elemental analysis: Calcd. C,71.63; H,6.83; N,7.59; Cl,9.61; Found C,66.73; H,6.32; N,7.01; Cl,8.98.

EXAMPLE 24

2-Methyl-4aα-(2-methoxyphenyl)-1,2,3,4,4a,5,11,11aβ-octahydroindolo[2,3-g]isoquinoline hydrochloride.

4.0 g (12.91 mmoles) of 2-methyl-4aα-(2-methoxyphenyl)-1,2,3,4,4a,5,6,7,8,8aβ-6-oxo-decahydroisoquinoline hydrochloride and 2.8 g (19.37 mmoles) of phenylhydrazine hydrochloride were reacted and worked-up as described in Example 3. The solid residue was purified by silica gel flash column chromatography, eluting with a mixture of CH$_2$Cl$_2$/MeOH/conc. NH$_4$OH 86:10:0.6 respectively, to afford 3.0 g of the free base, which was taken up in methanol and brought to acidic pH with HCl/Et$_2$O. The precipitate was filtered, washed and dried to yield 2.3 g of the title compound. M.P.=284°-286° C.

C$_{23}$H$_{26}$N$_2$O.HCl Elemental analysis: Calcd. C,72.14; H,7.11; N,7.32; Cl,9.26; Found C,72.18; H,7.10; N,7.30; Cl,9.21. I.R. (KBr): 3420; 3150; 1600; 1465; 1235; 1020 cm$^{-1}$ N.M.R. (CDCl$_3$) 80MHz (free base): δ7.7-6.6 (m,9H); 3.85 (s,3H); 3.2-2.5 (m,9H); 2.35 (s,3H); 2.0-1.75 (m,2H).

EXAMPLE 25

2-Methyl-4aα-(2-hydroxyphenyl)-1,2,3,4,4a,5,11,11aβ-octahydroindolo[2,3-g]isoquinoline hydrochloride.

900 mg (2.60 mmoles) of 2-methyl-4aα-(2-methoxyphenyl)-1,2,3,4,4a,5,11,11aβ-octahydroindolo[2,3-g]isoquinoline were reacted with 1.5 ml (15.6 mmoles) of boron tribromide as described in Example 1. The solid residue was purified by silica gel flash column chromatography, eluting with a mixture of CH$_2$Cl$_2$/MeOH/conc. NH$_4$OH 79:15:1 respectively, to afford 640 mg of the free base, which was taken up in a 4:1 mixture of acetone/methanol and brought to acidic pH with HCl/Et$_2$O. The precipitate was filtered, washed and dried to yield 545 mg of the title compound. M.P.=>300° C.

C$_{22}$H$_{24}$N$_2$O.HCl Elemental analysis: Calcd. C,71.63; H,6.83; N,7.59; Cl,9.61; Found C,70.95; H,6.83; N,7.39; Cl,9.43. I.R. (KBr): 3220; 3140; 1600; 1465; 1440; 1240 cm$^{-1}$

EXAMPLE 26

2-Methyl-4aα-(3-methoxyphenyl)-1,2,3,4,4a,5,12,12aβ-octahydroquino[2,3-g]isoquinoline.

4.7 ml of methanesulfonic acid were added to a mixture of 1.0 g (3.1 mmoles) of 2-methyl-4aα-(3-methoxyphenyl)-1,2,3,4,4a,5,6,7,8,8aβ-6-oxo-decahydroisoquinoline and 1.15 g (9.6 mmoles) of 2-aminobenzaldehyde in 32 ml of absolute ethanol. The solution was refluxed for 14 hours and the solvent was evaporated in vacuo. The residue was taken-up in saturated NaHCO$_3$ solution and AcOEt. The organic layer was dried over Na$_2$SO$_4$ and evaporated in vacuo. The solid residue was purified by silica gel flash column chromatography, eluting with CH$_2$Cl$_2$/MeOH/conc. NH$_4$OH 92:8:0.7 respectively, to afford 410 mg of the title compound. M.P.=159°-162° C.

C$_{24}$H$_{26}$N$_2$O I.R. (KBr): 2940; 2920; 1600; 1580; 1250 cm$^{-1}$ Elemental analysis: Calcd. C,80.41; H,7.31; N,7.82; Found C,79.50; H,7.30; N,7.49.

EXAMPLE 27

2-Methyl-4aα-(3-hydroxyphenyl)-1,2,3,4,4a,5,12,12aβ-octahydroquino[2,3-g]isoquinoline.

410 mg (1.14 mmoles) of 2-methyl-4aα-(3-methoxyphenyl)-1,2,3,4,4a,5,12,12aβ-octahydroquino[2,3-g]isoquinoline were reacted with 0.7 ml (6.84 mmoles) of boron tribromide as described in Example 1. The solid residue was purified by silica gel flash column chromatography eluting with CH$_2$Cl$_2$/MeOH/conc. NH$_4$OH 79:15:2 respectively, to yield 200 mg of the title compound. M.P.=275° C. dec.

C$_{23}$H$_{24}$N$_2$O I.R. (KBr): 2920; 2795; 1615; 1580; 1490; 1240 cm$^{-1}$ Elemental analysis: Calcd. C,80.20; H,7.02; N,8.13; Found C,80.06; H,7.10; N,8.06.

EXAMPLE 28

2-(2-Phenylethyl)-4aα-(3-methoxyphenyl)-1,2,3,4,4a,5,11,11aβ-octahydroindolo[2,3-g]isoquinoline.

670 mg (1.81 mmoles) of 2-(2-phenylethyl-4aα-(3-methoxyphenyl)-1,2,3,4,4a,5,6,7,8,8aβ-6-oxo-decahydroisoquinoline hydrochloride and 262 mg (1.81 mmoles) of phenylhydrazine hydrochloride were reacted and worked-up as described in Example 3.

The crude product was crystallized from a mixture of methanol/acetone to yield 680 mg of the title compound. M.P.=271°-275° C.

C$_{30}$H$_{32}$N$_2$O

EXAMPLE 29

2-(2-Phenylethyl)-4aα-(3-hydroxyphenyl)-1,2,3,4,4a,5,11,11aβ-octahydroindolo[2,3-g]isoquinoline.

680 mg (1.56 mmoles) of 2-(2-phenylethyl)-4aα-(3-methoxyphenyl)-1,2,3,4,4a,5,11,11aβ-octahydroindolo[2,3-g]isoquinoline were reacted with a 0.9 ml (9.36 mmoles) of boron tribromide as described in Example 1. The solid residue was purified by silica gel flash column chromatography, eluting with CH$_2$Cl$_2$/MeOH/conc. NH$_4$OH 94.5:5:0.5 respectively, to yield 180 mg of the title compound. M.P.=233°–236° C.

C$_{29}$H$_{30}$N$_2$O I.R. (KBr): 3400; 3305; 2920; 1580; 1450 cm$^{-1}$ Elemental analysis: Calcd. C,82.43; H,7.16; N,6.63; Found C,81.52; H,7.12; N,6.47.

EXAMPLE 30

2-Ethyl-4aα-(3-methoxyphenyl)-6-benzyl-1,2,3,4,4a,5,11,11aβ-octahydroindolo[2,3-g]isoquinoline.

680 mg (1.89 mmoles) of 2-ethyl-4aα-(3-methoxyphenyl)-1,2,3,4,4a,5,11,11aβ-octahydroindolo[2,3-g]isoquinoline, 85 mg (2.0 mmoles) of 60–65% NaH and 360 mg (2.0 mmoles) of benzylbromide were reacted as described in Example 8.

After the work-up, the crude product was crystallized from a mixture of methanol/acetone to yield 860 mg of the title compound. M.P.=283°–288° C.

C$_{31}$H$_{34}$N$_2$O

EXAMPLE 31

2-Ethyl-4aα-(3-hydroxyphenyl)-6-benzyl-1,2,3,4,4a,5,11,11aβ-octahydroindolo[2,3-g]isoquinoline.

860 mg (1.0 mmoles) of 2-ethyl-4aα-(3-methoxyphenyl)-6-benzyl-1,2,3,4,4a,5,11,11aβ-octahydroindolo[2,3-g]isoquinoline were reacted with 1.1 ml (11.4 mmoles) of boron tribromide as described in Example 1. The crude product was triturated in hot methanol, filtered, washed and dried to yield 380 mg of the title compound. M.P.=260°–262° C.

C$_{30}$H$_{32}$N$_2$O I.R. (KBr): 3020; 2940; 1580; 1470; 1235 cm$^{-1}$ Elemental analysis: Calcd. C,82.53; H,7.30; N,6.42; Found C,81.99; H,7.35; N,6.29.

EXAMPLE 32

2,6-Diethyl-4aα-(3-methoxyphenyl)-1,2,3,4,4a,5,11,11aβ-octahydroindolo[2,3-g]isoquinoline.

545 mg (1.51 mmoles) of 2-ethyl-4aα-(3-methoxyphenyl)-1,2,3,4,4a,5,11,11aβ-octahydroindolo[2,3-g]isoquinoline, 60 mg (1.6 mmoles) of 60–65% NaH and 181 mg (1.6 mmoles) of ethyl bromide were reacted as described in Example 8.

After the work-up, the crude product was crystallized from a mixture of methanol/acetone to yield 620 mg of the title compound. M.P.=277°–281° C.

C$_{26}$H$_{32}$N$_2$O

EXAMPLE 33

2,6-Diethyl-4aα-(3-hydroxyphenyl)-1,2,3,4,4a,5,11,11aβ-octahydroindolo[2,3-g]isoquinoline.

620 mg (1.6 mmoles) of 2,6-diethyl-4aα-(3-methoxyphenyl)-1,2,3,4,4a,5,11,11aβ-octahydroindolo[2,3-g]isoquinoline were reacted with 0.9 ml (9.6 mmoles) of boron tribromide as described in Example 1. The crude product was triturated in hot methanol, filtered, washed and dried to yield 250 mg of the title compound. M.P.=259°–262° C.

C$_{25}$H$_{30}$N$_2$O I.R. (KBr): 2980; 2920; 1610; 1580; 1455; 1350 cm$^{-1}$

EXAMPLE 34

2-n-Propyl-4aα-(3-methoxyphenyl)-1,2,3,4,4a,5,11,11aβ-octahydroindolo[2,3-g]isoquinoline hydrochloride.

900 mg (2.98 mmoles) of 2-n-propyl-4aα-(3-methoxyphenyl)-1,2,3,4,4a,5,6,7,8,8aβ-6-oxo-decahydroisoquinoline and 431 mg (2.98 mmoles) of phenylhydrazine hydrochloride were reacted and worked-up as described in Example 3. The solid residue was purified by silica gel flash column chromatography, eluting with a mixture of CH$_2$Cl$_2$/MeOH/conc. NH$_4$OH 93:7:0.5 respectively. The free base was dissolved in MeOH and the solution brought to acidic pH with HCl/Et$_2$O.

The precipitate was filtered, washed and dried to yield 420 mg of the title compound. M.P.=>300° C.

C$_{25}$H$_{30}$N$_2$O.HCl Elemental analysis: Calcd. C,73.06; H,7.60; N,6.82; Cl,8.63; Found C,72.31; H,7.51; N,6.78; Cl,8.10.

EXAMPLE 35

2-n-Propyl-4aα-(3-hydroxyphenyl)-1,2,3,4,4a,5,11,11aβ-octahydroindolo[2,3-g]isoquinoline hydrochloride.

420 mg (1.16 mmoles) of 2-n-propyl-4aα-(3-methoxyphenyl)-1,2,3,4,4a,5,11,11aβ-octahydroindolo[2,3-g]isoquinoline were reacted with 0.7 ml (6.84 mmoles) of boron tribromide as described in Example 1.

The solid residue was taken-up in methanol and the solution brought to acidic pH with HCl/Et$_2$O.

The precipitate was filtered, washed and dried to yield 190 mg of the title compound. M.P.=>300° C.

C$_{24}$H$_{28}$N$_2$O.HCl I.R. (KBr): 3455; 3260; 3200; 1600; 1455 cm$^{-1}$ Elemental analysis: Calcd. C,72.61; H,7.36; N,7.06; Cl,8.93; Found C,71.08; H,7.25; N,6,80; Cl,8.21.

EXAMPLE 36

2-Cyclopropylmethyl-4aα-(3-methoxyphenyl)-1,2,3,4,4a,5,11,11aβ-octahydroindole[2,3-g]isoquinoline hydrochloride.

800 mg (2.28 mmoles) of 2-cyclopropylmethyl-4aα-(3-methoxyphenyl)-1,2,3,4,4a,5,6,7,8,8aβ-6-oxo-decahydroisoquinoline and 340 mg (2.28 mmoles) of phenylhydrazine hydrochloride were reacted and worked-up as described in Example 3. The solid residue was purified by silica gel flash column chromatography eluting with a mixture of CH$_2$Cl$_2$/MeOH/conc. NH$_4$OH 93:7:0,5 respectively. The free base was dissolved in MeOH and the solution brought to acidic pH with HCl/Et$_2$O.

The precipitate was filtered, washed and dried to yield 360 mg of the title compound. M.P.=>300° C.

C$_{26}$H$_{30}$N$_2$O.HCl Elemental analysis: Calcd. C,73.82; H,7.39; N,6.62; Cl,8.38; Found C,73.48; H,7.25; N,6.58; Cl,8.01.

EXAMPLE 37

2-Cyclopropylmethyl-4 aα-(3-hydroxyphenyl)-1,2,3,4,4 a,5,11,11aβ-octahydroindolo[2,3-g]isoquinoline hydrochloride.

360 mg (0,93 mmoles) of 2-cyclopropylmethyl-4aα-(3-methoxyphenyl)-1,2,3,4,4a,5,11,11aα-octahydroindolo[2,3-g]isoquinoline were reacted with 0.57 ml (5.58 moles) of boron tribromide as described in Example 1.

The solid residue was taken-up in methanol and the solution brought to acidic pH with HCl/Et₂O.

The precipitate was filtered, washed and dried to yield 180 mg of the title compound. M.P.=>300° C.

$C_{25}H_{28}N_2O \cdot HCl$ I.R. (KBr): 3450; 3260; 3200; 1600; 1450 cm$^{-1}$ Elemental analysis: Calcd. C,73.42; H,7.15; N,6.85; Cl,8.67; Found C,72.91; H,6.81; N,6.51; Cl,8.09.

EXAMPLE 38

(+)-2-Ethyl-4aα-(3-methoxyphenyl)-1,2,3,4,4a,5,11,-11aβ-octahydroindolo[2,3-g]isoquinoline hydrochloride.

2.3 g {8.0 moles) of (−)-2-ethyl4aα-(3-methoxyphenyl)-1,2,3,4,4a,5,6,7,8,8aβ-6-oxo-decahydroisoquinoline and 1.17 g (8.1 mmoles) of phenylhydrazine hydrochloride were reacted and worked-up as described in Example 3. The solid residue was taken-up in 20 ml of acetone and the solution brought to acidic pH with HCl/Et₂O.

The precipitate was filtered, washed and dried to yield 1.36 g of the title compound. M.P.=274°-277° C.

$C_{24}H_{28}N_2O \cdot HCl$ $[\alpha]_D^{20}=+147.0$ (C=1 in MeOH) Elemental analysis: Calcd. C,72.61; H,7.36; N,7.06; Cl,8.93; Found C,72.44; H,7.37; N,7.01; Cl,8.92. The I.R. and N.M.R. spectra were identical to those obtained for the racemate.

EXAMPLE 39

(+)-2-Ethyl-4aα-(3-hydroxyphenyl)-1,2,3,4,4a,5,11,-11aβ-octahydroindolo[2,3-g]isoquinoline hydrochloride.

1.41 g (3.93 mmoles) of (+)-2-ethyl-4aα-(3-methoxyphenyl)-1,2,3,4,4a,5,11,11aβ-octahydroindolo[2,3-g]isoquinoline were reacted with 2.2 ml (23.58 mmoles) of boron tribromide as described in Example 1. The solid residue was taken-up in hot metanol and the solution was brought to acidic pH with HCl/Et₂O.

The precipitate was filtered, washed and dried to yield 0.95 of the title compound. M.P.=>300° C.

$C_{23}H_{26}N_2O \cdot HCl$ $[\alpha]_D^{20}=+141.1$ (C=1 in MeOH) Elemental analysis: Calcd. C,72.14; H,7.11; N,7.32; Cl,9.26; Found C,71.72; H,7.18; N,7.19; Cl,9.39. The I.R. and N.M.R. spectra were identical to those obtained for the racemate.

EXAMPLE 40

(−)-2-Ethyl-4aα-(3-methoxyphenyl)-1,2,3,4,4a,5,11,-11aβ-octahydroindolo[2,3-g]isoquinoline hydrochloride.

2.4 g (8.35 mmoles) of (+)-2-ethyl-4aα-(3-methoxyphenyl)-1,2,3,4,4a,5,6,7,8,8aβ-6-oxo-decahydroisoquinoline and 1.2 g (8.40 mmoles) of phenylhydrazine hydrochloride were reacted and worked-up as described in Example 3.

The solid residue was taken-up in 20 ml of acetone and the solution was brought to acidic pH with HCl/Et₂O. The precipitate was filtered, washed and dried to yield 1.55 g of the title compound. M.P.=273°-276° C.

$[\alpha]_D^{20}=-143.1$ (C=1 in MeOH) Elemental analysis: Calcd. C,72.61; H,7.36; N,7.06; Cl,8.93; Found C,72.38; H,7.41; N,7.00; Cl,9.00. The I.R. and N.M.R. spectra were identical to those obtained for the racemate.

EXAMPLE 41

(−)-2-Ethyl-4aα-(3-hydroxyphenyl)-1,2,3,4,4a,5,11,-11aβ-octahydroindolo[2,3-g]isoquinoline hydrochloride.

1.65 g (4.58 mmoles) of (−)-2-ethyl-4aα-(3-methoxyphenyl)-1,2,3,4,4a,5,11,11aβ-octahydroindolo[2,3-g]isoquinoline and 2.6 ml (27.50 mmoles) of boron tribromide were reacted as described in Example 1.

The solid residue was taken-up in hot methanol and the solution was brought to acidic pH with HCl/Et₂O.

The precipitate was filtered, washed and dried to yield 1.1 g of the title compound. M.P.=>300° C. $[\alpha]_D^{20}=-141$ 5 (C=1 in MeOH) Elemental analysis: Calcd. C,72.14; H,7.11; N,7.32; Cl,9.26; Found C,71.62; H,7.13; N,7,14; Cl,9.34. The I.R. and N.M.R. spectra were identical to those obtained for the racemate.

TABLE I

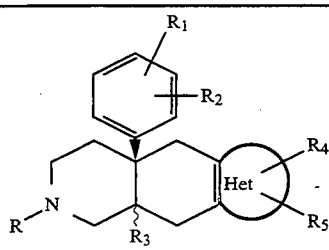

| | R | $R_1$ | $R_2$ | $R_3$ | Het | $R_4/R_5$ | Molecular Formula | Melting Point °C. | $[\alpha]_D^{20}$ C = 1, MeOH |
|---|---|---|---|---|---|---|---|---|---|
| Example 1 | $C_2H_5$ | m-OH | H | trans | 2,3-indole | H | $C_{23}H_{26}N_2O \cdot HCl$ | 277–278 | |
| Example 2 | $CH_3$ | m-OH | H | cis | 2,3-indole | H | $C_{22}H_{24}N_2O$ | 200–207 | |
| Example 3 | $C_2H_5$ | m-OCH₃ | H | trans | 2,3-indole | H | $C_{24}H_{28}N_2O \cdot HCl$ | 168–171 | |
| Example 4 | $CH_3$ | m-OCH₃ | H | cis | 2,3-indole | H | $C_{23}H_{26}N_2O$ | 202–206 | |
| Example 5 | $CH_3$ | m-OH | H | H-trans | 2,3-indole | H | $C_{22}H_{24}N_2O \cdot HCl$ | >300 | |
| Example 6 | $CH_3$ | m-OCH₃ | H | H-trans | 2,3-indole | H | $C_{23}H_{26}N_2O \cdot HCl \cdot \frac{1}{2}H_2O$ | >300 | |
| Example 7 | $CH_3$ | m-OH | H | H-trans | 2,3-indole | 6-CH₃ | $C_{23}H_{26}N_2O$ | 252–254 | |
| Example 8 | $CH_3$ | m-OCH₃ | H | H-trans | 2,3-indole | 6-CH₃ | $C_{24}H_{28}N_2O$ | 128–130 | |
| Example 9 | $CH_3$ | H | H | H-trans | 2,3-indole | H | $C_{22}H_{24}N_2$ | 221–223 | |
| Example 10 | $CH_3$ | m-OH | H | H-trans | 2,3-benzofuro | H | $C_{22}H_{23}NO_2$ | 258–261 | |
| Example 11 | $CH_3$ | m-OCH₃ | H | H-trans | 2,3-benzofuro | H | $C_{23}H_{25}NO_2 \cdot HCl$ | 246–248 | |
| Example 12 | $CH_3$ | m-OH | H | H-trans | 2,3-indole | 9-CH₃ | $C_{23}H_{26}N_2O$ | 292–296 | |
| Example 13 | $CH_3$ | m-OCH₃ | H | H-trans | 2,3-indole | 9-CH₃ | $C_{24}H_{28}N_2O \cdot HCl$ | 245–250 | |
| Example 14 | $CH_3$ | m-OH | H | H-trans | 2,3-indole | 9-F | $C_{22}H_{23}FN_2O$ | >300 | |
| Example 15 | $CH_3$ | m-OCH₃ | H | H-trans | 2,3-indole | 9-F | $C_{23}H_{25}FN_2O \cdot HCl$ | >300 | |
| Example 16 | $CH_3$ | m-OH | H | H-trans | 2,3-indole | 7-Cl | $C_{22}H_{23}ClN_2O$ | >300 | |

TABLE I-continued

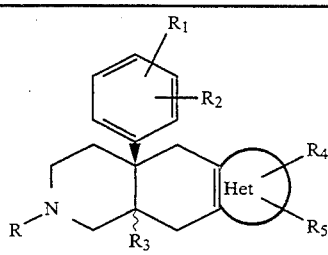

| | R | $R_1$ | $R_2$ | $R_3$ | Het | $R_4/R_5$ | Molecular Formula | Melting Point °C. | $[\alpha]_D^{20}$ C = 1, MeOH |
|---|---|---|---|---|---|---|---|---|---|
| Example 17 | $CH_3$ | m-$OCH_3$ | H | H-trans | 2,3-indole | 7-Cl | $C_{23}H_{25}ClN_2O \cdot HCl$ | >300 | |
| Example 18 | $CH_3$ | m-OH | H | H-trans | 2,3-indole | 9-Cl | $C_{22}H_{23}ClN_2O \cdot HCl$ | >300 | |
| Example 19 | $CH_3$ | m-$OCH_3$ | H | H-trans | 2,3-indole | 9-Cl | $C_{23}H_{25}ClN_2O \cdot HCl$ | >300 | |
| Example 20 | $C_2H_5$ | m-$OCH_3$ | H | H-trans | 2,3-indole | 6-$CH_3$ | $C_{25}H_{30}N_2O \cdot HCl$ | 234–240 | |
| Example 21 | $C_2H_5$ | m-OH | H | H-trans | 2,3-indole | 6-$CH_3$ | $C_{24}H_{28}N_2O \cdot HCl$ | >300 | |
| Example 22 | $CH_3$ | H | H | H-trans | 2,3-indole | 9-$OCH_3$ | $C_{23}H_{26}N_2O$ | 201–203 | |
| Example 23 | $CH_3$ | H | H | H-trans | 2,3-indole | 9-OH | $C_{22}H_{24}N_2O \cdot HCl$ | >300 | |
| Example 24 | $CH_3$ | o-$OCH_3$ | H | H-trans | 2,3-indole | H | $C_{23}H_{26}N_2O \cdot HCl$ | 284–286 | |
| Example 25 | $CH_3$ | o-OH | H | H-trans | 2,3-indole | H | $C_{22}H_{24}N_2O \cdot HCl$ | >300 | |
| Example 26 | $CH_3$ | m-$OCH_3$ | H | H-trans | 2,3-quinoline | H | $C_{24}H_{26}N_2O$ | 159–162 | |
| Example 27 | $CH_3$ | m-OH | H | H-trans | 2,3-quinoline | H | $C_{23}H_{24}N_2O$ | 275 dec. | |
| Example 28 | $PhCH_2CH_2$ | m-$OCH_3$ | H | H-trans | 2,3-indole | H | $C_{30}H_{32}N_2O$ | 271–275 | |
| Example 29 | $PhCH_2CH_2$ | m-OH | H | H-trans | 2,3-indole | H | $C_{29}H_{30}N_2O$ | 233–236 | |
| Example 30 | $C_2H_5$ | m-$OCH_3$ | H | H-trans | 2,3-indole | 6-$CH_2Ph$ | $C_{31}H_{34}N_2O$ | 283–288 | |
| Example 31 | $C_2H_5$ | m-OH | H | H-trans | 2,3-indole | 6-$CH_2Ph$ | $C_{30}H_{32}N_2O$ | 260–262 | |
| Example 32 | $C_2H_5$ | m-$OCH_3$ | H | H-trans | 2,3-indole | 6-$C_2H_5$ | $C_{26}H_{32}N_2O$ | 277–281 | |
| Example 33 | $C_2H_5$ | m-OH | H | H-trans | 2,3-indole | 6-$C_2H_5$ | $C_{25}H_{30}N_2O$ | 259–262 | |
| Example 34 | n-$C_3H_7$ | m-$OCH_3$ | H | H-trans | 2,3-indole | H | $C_{25}H_{30}N_2O \cdot HCl$ | >300 | |
| Example 35 | n-$C_3H_7$ | m-OH | H | H-trans | 2,3-indole | H | $C_{24}H_{28}N_2O \cdot HCl$ | >300 | |
| Example 36 | c-$C_3H_5CH_2$ | m-$OCH_3$ | H | H-trans | 2,3-indole | H | $C_{26}H_{30}N_2O \cdot HCl$ | >300 | |
| Example 37 | c-$C_3H_5CH_2$ | m-OH | H | H-trans | 2,3-indole | H | $C_{25}H_{28}N_2O \cdot HCl$ | >300 | |
| Example 38 | $C_2H_5$ | m-$OCH_3$ | H | H-trans | 2,3-indole | H | $C_{24}H_{28}N_2O \cdot HCl$ | 274–277 | +147.0 |
| Example 39 | $C_2H_5$ | m-OH | H | H-trans | 2,3-indole | H | $C_{23}H_{26}N_2O \cdot HCl$ | >300 | +141.1 |
| Example 40 | $C_2H_5$ | m-$OCH_3$ | H | H-trans | 2,3-indole | H | $C_{24}H_{28}N_2O \cdot HCl$ | 273–276 | −143.1 |
| Example 41 | $C_2H_5$ | m-OH | H | H-trans | 2,3-indole | H | $C_{23}H_{26}N_2O \cdot HCl$ | >300 | −141.5 |

PHARMACOLOGICAL DATA

RECEPTOR AFFINITY STUDY

Tissue preparation

Radio receptor binding to delta, mu and kappa sites is performed on fresh guinea pig brain homogenates prepared according to Kosterlitz (1981). Whole brain, without cerebellum is homogenized in 50 mM Tris-buffer and centrifuged at 49,000×g for 10 min.

The pellet is then resuspended in the s3me buffer, incubated at 37° C. for 45 min. and centrifuged again.

1.9 ml of the final homogenate (1:100 in Tris-pH 7.4 0° C.) is used for the binding assay.

Binding to delta sites

For binding experiments, $^3$H-DADLE, which binds to mu and delta sites, is used in the presence of 30 nM of unlabelled DAGO to prevent mu binding. A concentration of radioligand near $K_D$ is used in the binding assays evaluating compounds of the invention. Non-specific binding is determined by addition of Mr 2266, 2.5 μM. The tubes are incubated for 40 min at 25° C. and bound ligand is separated from free by filtration through Whatman GF-G filters. The level of bound radioactivity on the filters is measured by liquid scintillation after solubilization in filtercount. The equilibrium dissociation constant ($K_D$) and the maximum binding capacity ($B_{max}$) are determined from the analysis of saturation curves, while the inhibition constant ($K_i$) is determined from the analysis of competition experiments (Hill 1910; Scatchard 1949; Cheng and Prusoff 973; Gillan et al 1980).

Binding to mu sites (Magnan J., 1982)

$^3$H-[D-Ala$^2$, MePhe$^4$, Gly-Ol$^5$]Enkephalin ($^3$H-DAGO), an enkephalin analogue that binds selectively to mu receptor, is added to the biological substrate and incubated at 25° C. for 40 min, filtered through Whatman GF-C filters and washed with ice-cold Tris buffer. The filters are then dried, solubilized in Filtercount and the radioactivity monitored. Non-specific binding is determined in the presence of $10^{-6}$M naloxone.

Binding to kappa sites

The binding to the kappa site was performed using the highly selective kappa opioid ligand $^3$H-BRL 52537A (Sbacchi M, 1990). Final homogenate with solutions of the cold ligand and of the labelled ligand is incubated for 40 min. at 25° C., filtered through Whatman GF-C glass filter discs and washed. The radioactivity bound to the filters is counted by liquid scintillation spectrophotometry.

ANTINOCICEPTION

Tail-flick test in mice

The methodology employed is based on that described by D'Amour and Smith, J. Pharmacol. Exp. Ther. 72, 74 (1941).

Male Charles River mice (Swiss Strain) 29–35 g body weight are used.

Animals are allowed food and water ad libitum and are randomized into groups of 10 prior to experimentation. Before administration of the test compound, the reaction time of each animal is determined by focusing a beam of light onto the tail, eliciting a reflex withdrawal after a certain latency; only mice exhibiting a latency between 3–8 sec. are used subsequently in the evaluation of drug effects.

Test compounds are dissolved in either distilled water or distilled water plus 0.1M AMS and administered by the intrathecal route in a final volume of 5 μl/mouse, according to the method described by Hylden and Wilcox, Eur. J. Pharmacol. 67,313 (1980).

Four hours prior the beginning of experiments, mice are anaesthetized with pentobarbital (80 mg/Kg i.p.) and a caudal cutaneous incision (1 cm) is performed on the back using a disposable 30 gauge ½ inch needles mated to a 50 μl luer siringe (Hamilton). The drug are delivered intrathecally between L5 and L6 of spinous process.

Control animals receive 5 μJ/mouse of the appropriate vehicle alone. Following a pretreatment period of 10 min., the mice are again placed under the heat source and the reaction time redetermined.

Percentage quantal protection is determined as the number of mice in which the reaction time is doubled compared to pretreatment values, expressed as a percentage of the total number of mice in the group.

| PHARMACOLOGICAL TABLE | | | |
|---|---|---|---|
| | Opioid Receptor Binding | | Antinociception Mouse Tail-Flick |
| Example | $\delta$ KinM | $\mu$ | $\kappa$ | $ED_{50}$ mg/mouse i.t. |
| 1 | 16.4 | 2071 | >1000 | 0.010 |
| 5 | 16.0 | 309 | >1000 | |
| 7 | 33.6 | 306 | >1000 | |
| 10 | 10.1 | 104 | >1000 | |
| 12 | 61.9 | 678 | >1000 | |
| 16 | 16.4 | 568 | >1000 | |
| 39 | 6.24 | 2258 | >1000 | |

We claim:

1. A compound, or solvate or salt thereof, of formula (I):

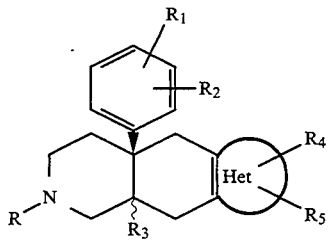

in which,
R is linear or branched $C_{1-5}$alkyl, $C_{3-7}$cycloalkyl, $C_{4-6}$cycloalkylalkyl, $C_{3-5}$alkenyl, aryl, aralkyl or furan-2-yl alkyl;
$R_1$ and $R_2$, which may be the same or different, are each hydrogen, hydroxy, $C_{1-3}$alkoxy, or halogen;
$R_3$ is hydrogen, hydroxy or $C_{1-3}$alkoxy; "Het" is indolo, N-methylindolo. N-ethylindolo, N-benzylindolo, benzofuro, benzothieno, quino or quinoxalino;
$R_4$ and $R_5$, which may be the same or different, are each hydrogen, $C_{1-3}$alkyl, halogen, nitro, 2. A compound according to claim 1, in which R is methyl, ethyl, cyclopropylmethyl, propyl, or 2-phenylethyl.

3. A compound according to claim 1, in which each of $R_1$ & $R_2$ is hydrogen, hydroxy or methoxy.

4. A compound according to claim 1 in which each of $R_4$ & $R_5$ is hydrogen, methyl, ethyl, fluorine, chlorine, hydroxy, methoxy or benzyl.

5. A compound selected from:
2-ethyl-4aα-(3-hydroxyphenyl)-1,2,3,4,4a,5,11,11aβ-octahydroindolo[2,3-g]isoquinoline;
2-methyl-4aα-(3-hydroxyphenyl)-1,2,3,4,4a,5,11,11aα-octahydroindolo[2,3-g]isoquinoline;
2-ethyl-4aα-(3-methoxyphenyl)-1,2,3,4,4a,5,11,11aβ-octahydroindolo[2,3-g]isoquinoline;
4aα-(3-methoxyphenyl)-2-methyl- 1,2,3,4,4a,5,11,11aα-octahydroindolo[2,3-g]isoquinoline;
2-methyl-4aα-(3-hydroxyphenyl)-1,2,3,4,4 a,5,11,11aβ-octahydroindolo [2,3-g]isoquinoline;
2-methyl-4a{x-(3-methoxyphenyl)-1,2,3,4,4a,5,11,11aβ-octahydroindolo [2,3-g]isoquinoline;
2,6-dimethyl-4a{x-(3-hydroxyphenyl)-1,2,3,4,4a,5,11,-11aβ-octahydroindolo[2,3-g]isoquinoline;
2,6-dimethyl-4aα-(3-methoxyphenyl)-1,2,3,4,4a,5,11,-11aβ-octahydroindolo[2,3-g]isoquinoline;
2-methyl-4aα-phenyl- 1,2,3,4,4a,5,11,11aβ-octahydroindolo[2,3-g]isoquinoline;
2-methyl-4aα-(3-hydroxyphenyl)-1,2,3,4,4a,5,11,11aβ-octahydrobenzofuro[2,3-g]isoquinoline;
2-methyl-4aα-(3-methoxyphenyl)-1,2,3,4,4a,5,11,11aβ-octahydrobenzofuro[2,3-g]isoquinoline;
2,9-dimethyl-4aα-(3-hydroxyphenyl)-1,2,3,4,4a,5,11,-11aβ-octahydroindolo[2,3-g]isoquinoline;
2,9-dimethyl-4aα-(3-methoxyphenyl)-1,2,3,4,4a,5,11,-11aβ-octahydroindolo[2,3-g]isoquinoline;
2-methyl-4aα-(3-hydroxyphenyl)-9-fluoro-1,2,3,4,4a,5,11,11aβ-octahydroindolo[2,3-g]isoquinoline;
2-methyl-4aα-(3-methoxyphenyl)-9-fluoro-1,2,3,4,5,11,11aβ-octahydroindolo[2,3-g]isoquinoline;
2-methyl-4aα-(3-hydroxyphenyl)-7-chloro-1,2,3,4,5,11,11aβ-octahydroindolo[2,3-g]isoquinoline;
2-methyl-4aα-(3-methoxyphenyl)-7-chloro-1,2,3,4,4a,5,11,11aβ-octahydroindolo[2,3-g]isoquinoline;
2-methyl-4aα-(3-hydroxyphenyl)-9-chloro-1,2,3,4,4a,5,11,11aβ-octahydroindolo[2,3-g]isoquinoline;
2-methyl-4aα-(3-methoxyphenyl)-9-chloro-1,2,3,4,4a,5,11,11aβ-octahydroindolo[2,3-g]isoquinoline;
2-ethyl-6-methyl-4aα-(3-methoxyphenyl)-1,2,3,4,4a,5,11,11aβ-octahydroindolo[2,3-g]isoquinoline;
2-ethyl-6-methyl-4aα-(3-hydroxyphenyl)-1,2,3,4,4a,5,11,11aβ-octahydroindolo[2,3-g]isoquinoline;
2-methyl-4aα-phenyl-9-methoxy-1,2,3,4,4a,5,11,11aβ-octahydroindolo[2,3-g]isoquinoline;
2-methyl-4aα-phenyl-9-hydroxy-1,2,3,4,4a,5,11,11aβ-octahydroindolo[2,3-g]isoquinoline;
2-methyl-4aα-(2-methoxyphenyl)-1,2,3,4,4a,5,11,11aβ-octahydroindolo[2,3-g]isoquinoline;
2-methyl-4aα-(2-hydroxyphenyl)-1,2,3,4,4a,5,11,11aβ-octahydroindolo[2,3-g]isoquinoline;
2-methyl-4aα-(3-methoxyphenyl)-1,2,3,4,4a,5,12,12aβ-octahydroquino[2,3-g]isoquinoline;
2-methyl-4aα-(3-hydroxyphenyl)-1,2,3,4,4a,5,12,12aβ-octahydroquino[2,3-g]isoquinoline;
2-(2-phenylethyl)-4aα-(3-methoxyphenyl)-1,2,3,4,4a,5,11,11aβ-octahydroindolo[2,3-g]isoquinoline;
2-(2-phenylethyl)-4aα-(3-hydroxyphenyl)-1,2,3,4,4a,5,11,11aβ-octahydroindolo[2,3-g]isoquinoline;

2-ethyl-4aα-(3-methoxyphenyl)-6-benzyl-1,2,3,4,4a,5,11,11aβ-octahydroindolo[2,3-g]isoquinoline;

2-ethyl-4aα-(3-hydroxyphenyl)-6-benzyl-1,2,3,4,4a,5,11,11aβ-octahydroindolo[2,3-g]isoquinoline;

2,6-diethyl-4aα-(3-methoxyphenyl)-1,2,3,4,4a,5,11,-11aβ-octahydroindolo[2,3-g]isoquinoline;

2,6-diethyl-4aα-(3-hydroxyphenyl)-1,2,3,4,4a,5,11,-11aβ-octahydroindolo[2,3-g]isoquinoline;

2-n-propyl-4aα-(3-methoxyphenyl)-1,2,3,4,4a,5,11,-11aβ-octahydroindolo[2,3-g]isoquinoline;

2-n-propyl-4aα-(3-hydroxyphenyl)-1,2,3,4,4a,5,11,-11aβ-octahydroindolo[2,3-g]isoquinoline;

2-cyclopropylmethyl-4aα-(3-methoxyphenyl)-1,2,3,4,4a,5,11,11aβ-octahydroindolo[2,3-g]isoquinoline;

2-cyclopropylmethyl-4au-(3-hydroxyphenyl)-1,2,3,4,4a,5,11,11aβ-octahydroindolo[2,3-g]isoquinoline;

6. A pharmaceutical composition comprising a compound according to any one of claim 1 and a pharmaceutically acceptable carrier.

7. A method for the treatment and/or prophylaxis of pain in mammals, which comprises administering to the mammal in need of such treatment and/or prophylaxis an effective amount of a compound according to claim 1.

8. A compound according to claim 2 wherein each of $R_1$ and $R_2$ is hydrogen, hydroxy or methoxy.

9. A compound according to claim 2 wherein each of $R_4$ and $R_5$ is hydrogen, methyl, ethyl, fluorine, chlorine, hydroxy, methoxy or benzyl.

10. A compound according to claim 2 wherein each of $R_1$ and $R_2$ is hydrogen, hydroxy or methoxy; Het is indolo, N-methylindolo, N-ethylindolo, N-benzylindolo, benzofuro, benzothieno, quino or quinoxaline; and each of $R_4$ and $R_5$ is hydrogen, methyl, ethyl, fluorine, chlorine, hydroxy, methoxy or benzyl.

11. A pharmaceutical composition comprising a compound according to claim 5 and a pharmaceutically acceptable carrier.

12. A method for the treatment or prophylaxis of pain in mammals, which comprises administering to a mammal in need thereof an effective amount of a compound according to claim 5.

* * * * *